United States Patent [19]
Makisumi et al.

[11] Patent Number: 4,576,956
[45] Date of Patent: Mar. 18, 1986

[54] IODO PROPARGYLAMINOISOXAZOLES AS FUNGICIDES

[75] Inventors: Yasuo Makisumi, Hyogo; Akira Murabayashi; Katsuya Tawara, both of Osaka; Yoshihachi Watanabe, Shiga; Toshio Takahashi, Hyogo; Takao Konishi, Osaka, all of Japan

[73] Assignee: Shionogi & Co., Ltd., Osaka, Japan

[21] Appl. No.: 530,883

[22] Filed: Sep. 9, 1983

[30] Foreign Application Priority Data

Oct. 5, 1982 [JP] Japan .................................. 57-176762

[51] Int. Cl.$^4$ ..................... A61K 31/41; C07D 261/12; C07D 261/20
[52] U.S. Cl. .................................... 514/380; 514/379; 548/246; 548/241; 548/243; 548/244; 548/245
[58] Field of Search ............... 548/241, 243, 245, 246; 424/272; 514/379, 380

[56] References Cited

U.S. PATENT DOCUMENTS 3,941,829 3/1976 Pissiotas et al. ..................... 424/278

FOREIGN PATENT DOCUMENTS

| 44008 | 1/1982 | European Pat. Off. | ............ 424/270 |
| 79862 | 7/1978 | Japan | .................... 548/241 |
| 4022365 | 2/1979 | Japan | .................... 424/272 |
| 8015965 | 1/1983 | Japan | .................... 424/267 |
| 419716 | of 1967 | Switzerland | ......................... 424/272 |

OTHER PUBLICATIONS

Nikles, Erwin, "(Propargylamino)phenyl Carbamate Pesticides," Chem. Abst. 71:70300n (1969).
Nikles, Erwin, "Substituted Aminophenyl Carbamates," Chem. Abst. 75:98341h (1971).
Krweger, et al., "Pesticidal Compositions," Chem. Abst. 88:33197q (1978).

Primary Examiner—Donald G. Daus
Assistant Examiner—G. Hendricks
Attorney, Agent, or Firm—Wenderoth, Lind & Ponack

[57] ABSTRACT

New (2-propynylamino)isoxazole and (3-iodo-2-propynylamino)isoxazole derivatives having anti-microbial activity which are used as active ingredients in anti-microbial compositions for medical use, for agricultural use and also for veterinary use.

21 Claims, No Drawings

IODO PROPARGYLAMINOISOXAZOLES AS FUNGICIDES

BACKGROUND OF THE INVENTION

This invention is in the field of propynylaminoisoxazole and 3-iodo-2-propynylaminoisoxazole derivatives which have anti-microbial activity.

In the prior art, 2-(3-halo-2-propynylthio)benzoxazoles have been known to have anti-fungal activity (Jap. Pat. Pub. (Kokoku) No. 26938/1971). There has also been known that 3-(3-iodo-2-propynyloxy)benzisoxazole has the same activity (Jap. Pat. Pub. (Kokai) No. 79862/1978). Besides, 3-(3-iodo-2-propynyl)oxy-5-methylisoxazole has been disclosed to be an anti-fungal and anti-septic agent for woods in Jap. Pat. Pub. (Kokai) No. 22365/1979. Meanwhile, (2-propynylamino)isoxazolesand (3-iodo-2-propynylamino)isoxazoles have neither been disclosed nor found ouit as anti-microbial agents. Additionally, the low toxicity has never been described in any literature.

SUMMARY OF THE INVENTION

An object of the present invention is to provide new (2-propynylamino)isoxazole derivatives and (3-iodo-2-propynylamino)isoxazole derivatives of the formula I:

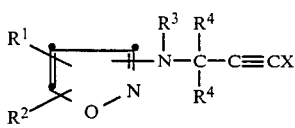

wherein
$R^1$ and $R^2$ each is hydrogen, $C_1$–$C_{10}$ alkyl, $C_1$–$C_4$ alkoxy, $C_3$–$C_6$ cycloalkyl, halogen, A—$CH_2$—, B—, B—$CH_2$— or B—$CH_2O$— wherein A is $C_1$–$C_4$ alkoxy or mono- or di-$C_1$–$C_4$ alkylamino and B is phenyl, furyl, thienyl or imidazolyl optionally substituted by one or two groups selected from the group consisting of halogen and carboxy; $R^1$ and $R^2$ when taken together may form $C_2$–$C_5$ alkylene; $R^3$ and $R^4$ each is hydrogen or $C_1$–$C_4$ alkyl; and X is hydrogen or iodine.

A further object of this invention is to provide an anti-microbial composition containing the above derivative, which is applied for medical use, agricultural use and also for veterinary use. Another object of this invention is to provide methods for protecting and treating human beings and domestic animals as well as agricultural and horticultural products with the anti-microbial compositions.

DETAILED DESCRIPTION OF THE PREFERRED EMBODIMENT

This invention relates to novel propynylaminoisoxazole derivatives, more particularly isoxazole derivatives substituted by 2-propynylamino or 3-iodo-2-propynylamino at the 3, 4 or 5 position.

In these days, many penicillins and cephalosporins have been studied and developed and a number of drugs against both gram-positive and gram-negative bacteria have been introduced on the market. On the contrary, there has been an increase in dermatomysis and mycosis of the internal organs caused by profunda fungi, which are hardly remedial.

The fungicides on the market, however, can merely be applied in a restricted manner because of their side effects. Accordingly, the development of a new fungicide which is devoid of such side-effects is still awaited.

The desired compound of this invention is represented by the formula I noted above.

In the definition, "$C_1$–$C_4$ alkyl" includes straight-chain and branched alkyls containing 1 to 4 carbon atoms such as methyl, ethyl, propyl, isopropyl, butyl and t-butyl. "$C_1$–$C_{10}$ Alkyl" includes straight-chain and branched $C_5$–$C_{10}$ alkyls such as heptyl, hexyl, octyl, nonyl and decyl in addition to the above $C_1$–$C_4$ alkyl. Besides, when one of $R^1$ or $R^2$ is a higher alkyl, the other and $R^3$ and $R^4$ should be selected from the groups of low carbon number and sterically less hindrance.

"$C_1$–$C_4$ Alkoxy" includes straight-chain and branched alkyloxy such as methoxy, ethoxy, propoxy, isopropoxy and butoxy. "$C_3$–$C_6$ Cycloalkyl" includes, for example, cyclopropyl, cyclobutyl, cyclopentyl, cyclohexyl and the like. "Mono and di-$C_1$–$C_4$ alkylamino" means an amino group substituted by one or two $C_1$–$C_4$ alkyls noted above. "$C_2$–$C_5$ Alkylene" includes both straight-chain and branched alkylenes having 2 to 5 carbon atoms such as methylene, ethylene, trimethylene, propylene, tetramethylene and ethylethylene.

$R^1$ and $R^2$ may be B, B—$CH_2$— or B—$CH_2O$— wherein B is phenyl, furyl, thienyl or imidazolyl substituted by one or two groups selected from the group consisting of halogen and carboxy. It means that $R^1$ and $R^2$ may be phenyl, furyl, thienyl, imidazolyl, benzyl, furylmethyl, thienylmethyl, imidazolylmethyl, benzyloxy, furylmethoxy, thienylmethoxy and imidazolylmethoxy and the present ring may optionally be substituted by a carboxy, a halogen, two carboxys or two halogens, practically, a carboxy, an iodine, two iodines, a bromine, two bromines, a chlorine, two chlorines, a fluorine or two fluorines.

Preferably, $R^1$ is hydrogen, $C_1$–$C_{10}$ alkyl, specifically $C_1$–$C_4$ alkyl, $C_3$–$C_6$ cycloalkyl and optionally substituted phenyl and optionally substituted thienyl, more practically $C_1$–$C_4$ alkyl, $C_3$–$C_6$ cycloalkyl, phenyl and thienyl, most practically methyl, isopropyl, 2-thienyl and phenyl. Preferably $R^2$ is hydrogen, $C_1$–$C_4$ alkyl and halogen, more specifically hydrogen, methyl and chlorine. Preferably $R^1$ and $R^2$ when taken together are tetramethylene. Preferably $R^3$ is hydrogen, methyl and ethyl, more specifically hydrogen and methyl. Preferred $R^4$ is hydrogen and methyl, more specifically hydrogen.

The group

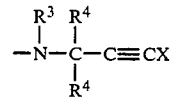

is located preferably at the position 3 or 5 of the isoxazole ring.

The desired compound (I) can be prepared by various methods, one of which is illustrated as follows:

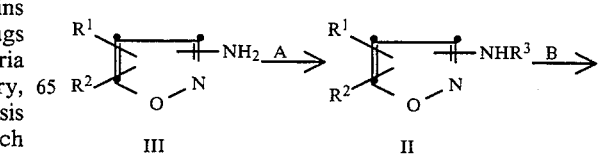

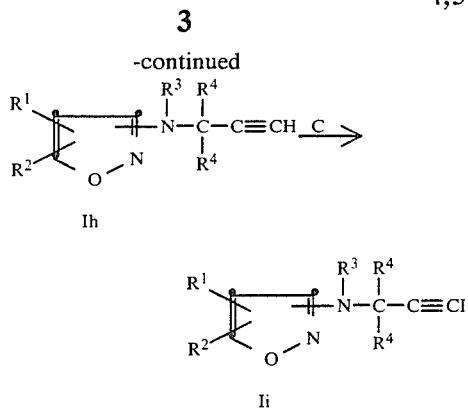

wherein $R^1$, $R^2$, $R^3$ and $R^4$ each has the same meaning as noted above.

Step A

In this step a desired $R^3$ is introduced to a starting compound, aminoisoxazole (III). The amino group may be protected by a suitable group before the reaction to avoid being substituted by two $R^3$ groups. The step is naturally skipped when a desired compound has no substituent at the amino group; i.e. $R^3$ is hydrogen. cl

Step B

In this step, 2-propynyl group is introduced into the mono-substituted amino group. A 1,1-dialkylated 2-propynyl group may be used when desired. The amino protecting group should be removed before the step when the amino group is substituted by both an alkyl ($R^3 \neq H$) and a protecting group. On the contrary, the amino group should be protected by a protecting group if it is desirable that $R^3$ is hydrogen, and the protecting group should be removed after the reaction.

Step C

This step consists in iodination of the γ carbon of the 2-propynyl group.

The substituents, $R^1$ and $R^2$ can be introduced to the isoxazole ring at a suitable stage before and after these A, B and C steps.

In effect, the reactions in the above steps are monosubstitution of the amino group and iodination of the γ carbon of the propynyl group. The introduction of an amino-protecting group is effected by the usual methods. The reaction is carried out with an acyl halide (e.g. acetyl chloride, and ethoxycarbonyl chloride) or an alkoxyalkyl halide (e.g. methoxymethyl chloride) in an inert solvent (e.g. ethers, benzenes, halogenohydrocarbons and esters) in the presence of a base (e.g. pyridine) at room temperature or under heating. The removal of the amino-protecting group is effected with an acid (e.g. hydrochloric acid) or an alkali (e.g. sodium hydroxide) in the usual manner. The introduction of a 2-propynyl group and an $R^3$(=alkyl) is carried out with the corresponding halide or dialkyl sulfonate. An alkyl halide or a 2-propynyl halide is reacted with Compound III or II in an inert solvent in the presence of a base (e.g. sodium hydride, butyllithium, potassium hydroxide and sodium hydroxide) at a temperature of from ice-cooling temperature to room temperature. The inert solvent includes the organic solvents exemplified in the above and dimethylformamide; practically dimethylformamide is preferred. The reaction is carried out with an alkali hydroxide (e.g. potassium hydroxide and sodium hydroxide) in an inert solvent (e.g. methylene chloride, chloroform and benzene) in the presence of a usual phase transfer reagent (e.g. benzyl triethyl ammonium chloride and tetrabutyl ammonium chloride) usually at room temperature. The reaction may be carried out under cooling or with heating. 2-Propynyl group can be introduced with a phase transfer reagent in the same manner.

The resulting (2-propynylamino)isoxazole (Ih) is further reacted with iodine, if desired, to give (3-iodo-2-propynylamino)isoxazole (Ii). The iodination is effected in the usual manner. Compound (Ih) is reacted with iodine in an inert solvent in the presence of an alkali metal compound (e.g. sodium hydroxide and butyllithium) under cooling or at room temperature. The reaction proceeds smooth in an aqueous or anhydrous alcohol in the presence of an alkali metal hydroxide or in tetrahydrofuran or an ether in the presence of an alkyllithium.

The thus-prepared Compounds (Ih) and (Ii) show antimicrobial activity against pathogenic microorganisms to human beings, domestic animals and agricultural, horticulclual and forest products. Compounds (Ih) is also useful as an intermediate for Compound (Ii) since the later has stronger anti-microbial activity than the former.

Some test data are shown below with respect to the anti-fungal activity of some typical compounds.

Test A-1 Anti-fungal Activity (MIC)

The following results (Table 1) were obtained in an anti-fungal activity test in vitro against *Aspergillus fumigatus*, *Candida albicans* M-9 and *Trichophyton asteroides*. The concentration of the test cells was $1 \times 10^5$ cells/ml and the activity was measured by a microwell dilution method. The structure of the test compounds is referred to in the Examples.

Test A-2 Anti-fungal Activity (MCC)

Some MCC (Minimal Cidal Concentration) values (Table 1) were obtained against *Candida albicans* and *Trichophyton asteroides* by the following method. After the MIC value was obtained by the microwell method, a loopful amount was picked up from the medium in which no growth of the fungus was observed, inoculated into a Subrouraud's glucose agar medium and incubated at 28° C. for 2 days in the case of *C. albicans* and for 7 days in the case of *T. asteroides*. The minimum concentration at which the fungi did not grow was recognized as MCC value.

TABLE 1

| Comp. No. | MIC (γ/ml) | | | MCC (γ/ml) | |
|---|---|---|---|---|---|
| | A. fumigtus | C. albicans M-9 | T. asteroides | C. albicans | T. asteroides |
| 1 | 6.3 | 3.1 | 0.8 | — | — |
| 2 | 6.2 | 0.1 | 0.4 | — | — |
| 3 | 0.8 | 0.4 | 1.6 | — | — |
| 4 | 1.6 | 0.8 | 1.6 | 25 | 3.1 |
| 5 | 1.6 | 0.8 | 1.6 | — | — |
| 6 | 1.6 | 0.8 | 1.6 | 25 | 3.1 |
| 8 | 1.6 | 0.8 | 3.1 | — | — |
| 10 | 1.6 | 0.8 | 0.8 | — | — |
| 11 | 3.1 | 0.8 | 1.6 | 12.5 | 1.6 |
| 13 | 3.1 | 3.1 | 3.1 | — | — |
| 19 | 3.1 | 0.8 | 0.8 | — | — |
| 20 | 0.8 | 0.8 | 0.8 | 50 | 3.1 |
| 21 | 1.6 | 1.6 | 1.6 | — | — |
| 24 | 0.8 | 0.2 | 0.4 | 12.5 | 3.1 |
| 26 | 50 | 6.3 | 1.6 | — | — |
| 32 | 1.6 | 1.6 | 3.1 | — | — |
| 33 | 3.1 | 1.6 | 0.8 | — | — |

TABLE 1-continued

| Comp. No. | MIC (γ/ml) | | | MCC (γ/ml) | |
|---|---|---|---|---|---|
| | A. fumigtus | C. albicans M-9 | T. asteroides | C. albicans | T. asteroides |
| 38 | 3.1 | 0.8 | 0.8 | — | — |
| Ref. Comp. | 12.5 | 6.3 | 0.2 | >100 | 6.3 |

Ref. Comp. = Clotrimazole

Test B-1 Control Test of Botrytis Rot (Gray Mold) of Cucumber

Seedlings of Cucumber (Cultivar: Matsukaze) were planted and grown in soil in vinyl-chloride cups of 9 cm in diameter in a greenhouse. At the primary leaf stage, 2.5 ml each of a solution containing a prescribed concentration of a test compound was applied over the above cucumbers having been kept at 25°–26° C. for 1 day. Five pieces of absorbent cotton of 6 mm in diameter were put on a primary leaf and a spore suspension of *Botrytis cinerea* was inoculated dropwise onto the cotton. The treated cucumbers were kept for 3 days in a greenhouse (20° C.) and then disease degrees were counted.

Standard of Evaluation (1) No disease ... × 0
(2) A slight soaked lesion on the reverse of the test leaf ... × 5
(3) A slight fade of the leaf ... × 10
(4) The inoculated part was faded and the fading expanded erosively ... × 20

Disease Degree =

$$\frac{20 \times (4) + 10 \times (3) + 5 \times (2) + 0 \times (1)}{20 \times \text{Cotton piece Number}} \times 100$$

Percent Disease Control (%) =

$$\frac{\text{Disease Degree in Untreated Plot} - \text{Disease Degree in Treated Plot}}{\text{Disease Degree in Untreated Plot}} \times 100$$

Result

TABLE 2

| Comp. No. | Concentration (ppm) | Percent Disease Control (%) |
|---|---|---|
| 1 | 500 | 100 |
| 5 | 500 | 100 |
| 11 | 500 | 100 |
| 15 | 500 | 100 |
| 24 | 500 | 100 |
| 32 | 500 | 100 |
| 34 | 500 | 100 |
| Untreated | — | 0 |

Test B-2 Control Test to Sclerotinia Rot of Cucumber

Cucumber seedlings were sprayed with 2.5 ml of a test solution in the same manner as in Test B-1. After the spraying, the seedlings were kept at 25°–26° C. for a day and three disks of 4 mm in diameter containing mycelia of *Sclerotinia sclerotiorum* were put on a primary leaf and then 10 μl of PD broth were dropped on the disks. The treated seedlings were kept in a greenhouse (20° C.) for 2 days and then the diameters of the disease spots were measured by a pair of slide callipers.

Percent Disease Control (%) =

$$\frac{\text{Diameter of Disease Spots of Untreated Plot} - \text{Diameter of Disease Spots of Treated Plot}}{\text{Diameter of Disease Spots of Untreated Plot}} \times 100$$

Result

TABLE 3

| Comp. No. | Concentration (ppm) | Percent Disease Control (%) |
|---|---|---|
| 1 | 500 | 100 |
| 5 | 500 | 100 |
| 6 | 500 | 100 |
| 19 | 500 | 100 |
| 20 | 500 | 100 |
| 24 | 500 | 100 |
| 32 | 500 | 100 |
| 33 | 500 | 100 |
| Untreated | — | 0 |

Test B-3 Control Test to Downy Mildew of Cucumber

Each cucumber seedling was sprayed with 2.5 ml of a test solution in the same manner as in Test B-1. After the spraying, the seedlings were kept at 25°–26° C. for a day and a zoosporangium suspension or *Pseudoperonospora cubensis* was inoculated at a rate of five spots per leaf on a primary leaf. The treated seedlings were kept in a greenhouse for 7 days and then observed.

Standard of Evaluation (1) No Disease ... X0
(2) Slight disease at the inoculation spot ... X5
(3) A disease spot in the same size as the inoculation spot (without spreading) ... x10
(4) A disease spot larger than the inoculation spot ... x20

Disease degree and percent disease control were calculated in the same manner as in Test B-1.

Result

TABLE 4

| Comp. No. | Concentration (ppm) | Percent Disease Control (%) |
|---|---|---|
| 1 | 500 | 100 |
| 5 | 500 | 95.0 |
| 9 | 500 | 100 |
| 26 | 500 | 100 |
| 33 | 500 | 100 |
| 34 | 500 | 100 |
| Untreated | — | 0 |

Test B-4 Control Test to Anthracnose of Cucumber

Each cucumber seedling was sprayed with 2.5 ml of a test solution in the same manner as in Test B-1. After the spraying, the seedlings were kept at 25°–26° C. for a day and were inoculated with five filter-paper disks of 6 mm in diameter saturated with a conidium suspension of *Colletotrichum lagenarium* at a concentration of 1×10⁶ conidia/ml. The treated seedlings were kept in a greenhouse (25° C.) for 3 days and further kept at below 25° C. for 3 days.

Standard of Evaluation

The same as noted in Test B-3.

Result

TABLE 5

| Comp. No. | Concentration (ppm) | Percent Disease Control (%) |
| --- | --- | --- |
| 1 | 500 | 100 |
| 6 | 500 | 100 |
| 19 | 500 | 100 |
| 26 | 500 | 100 |
| 34 | 500 | 100 |
| Untreated | — | 0 |

Test B-5 Control Test to Powdery Mildew of Cucumber

Each cucumber seedling was sprayed with 2.5 ml of a test solution. The seedlings were kept at 25°–26° C. for 1 day after the spraying and then sprayed with a conidium ($1 \times 10^5$ conidia/ml) of Sphaerotheca fuliginea in a 100 ppm spreader solution (containing 20% polyoxyethylene glycol alkyl phenol ether and 12% lignin sulfonate) at a rate of 25 ml/20 cups.

The seedlings were kept in a greenhouse (25° C.) for 2 weeks and then observed.

Standard of Evaluation $$\text{Disease Degree} = \frac{\text{Diseased Area}}{\text{Leaf Area}} \times 100$$

The percent disease control was calculated in the same manner as in Test B-1.

Result

TABLE 6

| Comp. No. | Concentration (ppm) | Percent Disease Control (%) |
| --- | --- | --- |
| 1 | 500 | 100 |
| 24 | 500 | 100 |
| 26 | 500 | 100 |
| 32 | 500 | 100 |
| Untreated | — | 0 |

Test B-6 Control Test to Damping-off of Cucumber

Twenty cucumber seeds were sown into sterilized soil (150 ml) in a pot of 9 cm in diameter. The fungi, Phythium aphanidermatum, Fusarium oxysporum and Rhizoctonia solani were cultured on a wheat bran medium for 5 days and an additional 2 days thereafter were mixed with sterilized soil. The surface of the sown spots was covered with the above culture medium. A test solution (30 ml) at a prescribed concentration was poured into each pot. The pots were kept in a greenhouse (28° C.) for 1 week in the case of Pythium and Rhizoctonia and for 2 weeks in the case of Fusarium.

The disease degree was observed and percent disease degree was calculated by the following formula:

Standard of Evaluation (1) No germination . . . x 4
(2) Germed but withered . . . x 3
(3) Disordered in 1/3 or more . . . x 2
(4) Disordered in less than 1/3 . . . x 1
(5) Not damaged . . . x 0

Percent Disease Degree =

-continued
$$\frac{4 \times (1) + 3 \times (2) + 2 \times (3) + 1 \times (4) + 0 \times (5)}{\text{Seed Number} \times 4} \times 100$$

The percent disease control was calculated in the same manner as in Test B-1.

Result

TABLE 7

| Comp. No. | Concentration (ppm) | Percent Disease Control (%) | | |
| --- | --- | --- | --- | --- |
| | | P* | F* | R* |
| 19 | 500 | 100 | 78 | 100 |
| 20 | 500 | 100 | 57 | 100 |
| 24 | 500 | 100 | 93 | 100 |
| 32 | 500 | 100 | 50 | 100 |
| Untreated | — | 0 | 0 | 0 |

P* = Pythium aphanidermatum
F* = Fusarium oxysporum
R* = Rhizoctonia solani

Test B-7 Control Test to Blast of Rice Plant

Seedlings of rice plant (cultivar: Aichi-asahi) grown in a greenhouse for 10 days were transplanted in a vinyl chloride-cup of 12 cm in diameter. A test solution at a prescribed concentration was sprayed to the rice plants 14 days after the transplanting. One day after the treatment, a spore suspension of Pyricularia oryzae was sprayed on the rice plants, which were kept at 27° C. in 95-98% humidity for 24 hours and then kept at 26° C. in 90% humidity for 7 days in a greenhouse. The number of infected spots was counted and the percent disease control was calculated in the same manner as in Test B-1.

Result

TABLE 8

| Comp. No. | Concentration (ppm) | Percent Disease Control (%) |
| --- | --- | --- |
| 13 | 500 | 99 |
| 19 | 500 | 100 |
| 20 | 500 | 100 |
| 27 | 500 | 100 |
| 32 | 500 | 98 |
| 36 | 500 | 90 |
| Untreated | — | 0 |

Compounds (I) tested above shows anti-fungal activity against phathogenic fungi in the above tests. Compounds (I) other than the above have also anti-fungal activity and anti-bacterial activity and are usable as anti-microbial agents in the medical field and in the agricultural, horticultural and forestry field.

As Compound(I) is active against veterinary phathogenic microorganisms, it is applicable to prevent and treat infections of domestic animals and fishes. More practically, Compound (I) can be prescribed for infections of chickens, pigs, cattle and the like such as coccidiosis, mycoplasmosis, bacterial diarrhea, enzootic pneumonia, dysentery, atrophic rheritis and atypical microbacteriosis. Additionally, it may be used to prevent and treat pseduotubelucurosis of yellowtails, red disease of Japanese eels and the like. Some test results shown below afford an example.

(1) Compounds 26, 29 and 34 inhibit the growth of a causative protozoa, Eimeria tenella at a concentration of 0.1–10 ppm.

(2) Compounds 9, 27, 28 and 29 inhibit the growth of a diarrhea-causative bacteria, *Staphylococcus aureus* 209 at a concentration of 0.78u–3.13 ppm.

(3) The minimum inhibition concentration of Compounds 5, 19 and 20 is 6.25–12.5 ppm against *Mycoplasma gallisepticum*.

(4) Compounds 9, 13, 15 and 34 inhibit the growth of a swine enzootic pneumonia-causative bacteria, *Mycoplasma hyopneumonia* at a concentration of 3.13–12.5 ppm.

As noted above, Compound (I) is usable as an active ingredient of anti-microbial composition for medical, agricultural or veterinary use, wherein the term "agricultural" includes agricultural, horticultural and forestry and the term "veterinary" includes veterinary and piscicultural, specifically containing an effective amount of Compound (I).

Compound (I), when used as medicine, is mixed, dissolved and formulated with pharmaceutically accepted suitable adjuvants such as carriers, diluents, flavorings, aromatics and surfactants to give tablets, capsules, powders and the like for oral administration and injection, ointment, suppositories and the like for parenteral administration. The external application is preferred.

The dosage to be administered is determined depending on the kind of the diseases, the age and body weight of the patient and the like. The amount is, for example, about 100 mg to about 500 mg per day for an adult patient when Compound (I) is administered orally.

Compound (I) is formulated into an anti-microbial composition for agricultural use comprising as an active ingredient about 0.01 to about 90 weight percent of Compound (I) to the whole by mixing with a suitable solid or liquid carrier and other suitble adjuvants such as surfactants, diluents, spreaders and synergists. Solid carriers include talc, clay, bentonite, pyrophyllite, kaolin, diatomaceus earth, silica and the like. Liquid carriers include water, methanol, ethanol, acetone, dimethyl formamide, ether, benzene, xylene, toluene, naphtha and the like. Surfactants include non-ionic surfactants (e.g. polyoxyethylene alkyl phenyl ethers and polyoxyethylene fatty acid esters), anionic surfactants (e.g. alkylbenzene sulfonic acid salts, lignin sulfonic acid salts and dinaphthylmethane sulkfonic acid salts, polyvinyl alcohols, CMC, gum arabic and the like.

The anti-microbial composition is formulated into powders, wettable powders, granules, emulsions, suspensions, solutions and the like and used for sterilizing agricultural products, seedlings, seeds and the like as well as soil. Compound (I), for example, is homogeneously dissolved in a hydrocarbon or an alcohol with a suitable surfactant to give an emulsion or a solution. It is mixed with a mineral powder and a suitable surfactant, crushed and homogenized to fine powder to a give a wettable powder. The thus-prepared composition is diluted with water to a desired concentration and sprayed. Alternatively, it may be diluted with mineral powder, homogeneously crushed, blended and used as a dust. The composition can be combined with other agrochemicals, e.g. insecticides, sterilizers, herbicides, plant-growth regulators, miticides and the like. Further, it can also be mixed with nutrients. The composition may be usually used at a concentration of about 50 to about 1000 ppm of Compound (I) when sprayed onto agricultural products.

Compound (I), when used as an active ingredient of an anti-microbial composition for veterinary use, can be used singly or as a mixture with suitable adjuvants utilized in this field. The composition comprises an antimicrobially effective amount of Compound (I) as an active ingredient. Practically, it may comprise as an active ingredient about 0.01 to about 90 weight percent of Compound I to the whole. Additionally, disintegrating agents, lubricants, stabilizers, flavorings, wetting agents, coloring agents, preservatives, aromatics and the like may be added, if necessary, to give powders, dusts, granules, solutions, suspensions, premixes, capsules, emulsions, tablets and the like. Carriers are selected from those generally used in poultry drugs, for example, water, lactose, sucrose, talc, colloidal silica, soybean, brewer's grain, starch, yeast, wheat, defatted rice bran, defatted soybean, corn, wheat bran and other commercially available feed for domestic animals and poultry.

The method for protecting domestic animals, poultry and fishes from microbial infections and treating them for the infections is as follows:

The anti-microbial composition can be mixed with feed or dissolved into drinking water for domestic animals or dissolved into water used for maintaining fish; otherwise, it can be orally administered to domestic animals and poultry. The composition is preferably applied to domestic animals (e.g. chickens, ducks, turkeys, swine, and cattle) and edible fish. Solutions, suspensions, emulsions and the like are conveniently used for mixing with feed and dissolving in water. Capsules and tablets are suitable for oral administration. Ointments and suppositories are usable for parenteral administration. Compound I is added, for example, in a proportion of about 0.001 to about 0.05 weight percent to the feed and in a proportion of about 0.0005 to about 0.03 weight percent to drinking water. It is orally administered at about 20 to 200 mg/kg body weight at a time. The dosge noted above varies depending on the applied subject, purpose, seriousness of the disease and the like. Other anti-microbial agents for domestic animals and poultry can be mixed with the composition, if desired. Additionally, ointments containing the composition are effectively applied to the external diseases of domestic animals and poultry.

Furthermore, Compound I may be used as an active ingredient of sterilizers for painting, timber, paper, cloth and the like. For example, an effective amount of Compound I may be mixed in a paint for ships to prevent the adherence of shellfish and algae. A sterilizer containing containing I at an effective concentration may be sprayed to wall-paper and wall-cloth.

The following examples are included merely to aid in the understanding of the invention and variations may be made by one skilled in the art without departing from the spirit and scope of the invention.

EXAMPLE 1

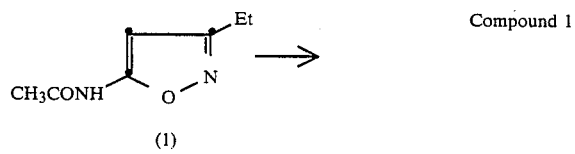

Compound 1

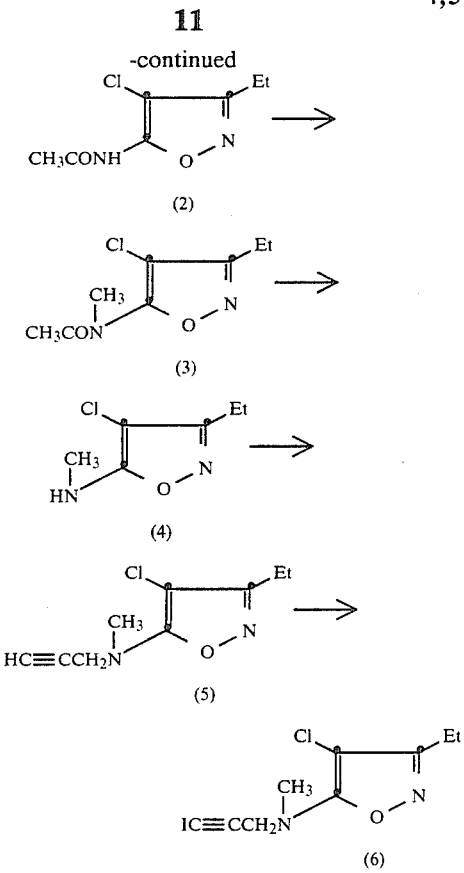

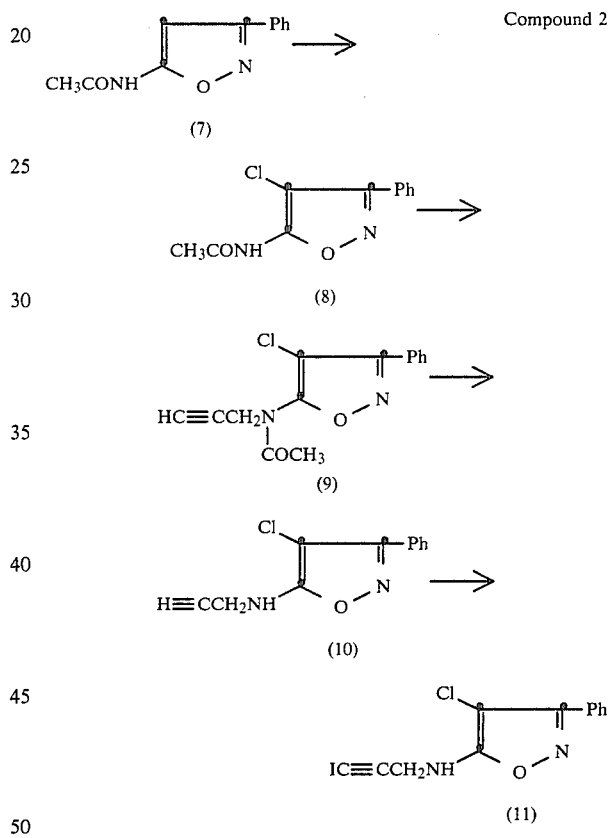

)aminoisoxazole (5) (746 mg) was obtained from chloroform fractions. NMR $\delta_{CDCl_3}$ 1.25t(J=7 Hz), 2.55q (J=7 Hz), 2.32t (J=2 Hz), 3.12s, 4.18d (J=2 Hz).

(v) Compound (5) (746 mg) was dissolved in a mixture of methanol (10 ml) and 5N sodium hydroxide (1.65 ml), iodine (1.43 g) was added thereto and stirred at room temperature for 10 minutes. The mixture was extracted with ether after addition of water and 1% sodium thiosulfate. The extract was washed with water, dried and evaporated to give 3-ethyl-4-chloro-5-(N-methyl-N-3-iodo-2-propynyl)-aminoisoxazole (6) (1.215 g); mp. 80°–81° C. (recrystallized from ether-hexane).

Elementary Analysis: Calcd. for $C_9H_{10}N_2OClI$: Calcd. (%): C, 33.31; N, 3.11; N, 8.63; Cl. 10.92; I, 39.10, Found (%): C, 33.17; H, 3.21; N, 8.78; Cl. 10.86; I, 39.02.

EXAMPLE 2

(i) 3-Ethyl-5-acetylaminoisoxazole (1) (1.98 g) was dissolved in acetic acid (15 ml), chlorine-tetrachloromethane (18 ml, containing 1.09 g of chlorine) was added thereto under stirring at room temperature and after addition of water the mixture was extracted with chloroform after 5 minutes. The extract was washed with water, dried over sodium sulfate and evaporated. The resulting crystalline residue was recrystallized from ether/hexane to give 3-ethyl-4-chloro-5-acetylaminoisoxazole (2) (1.86 g), mp. 113°–114° C.

(ii) Compound (2) (1.08 g) was dissolved in chloroform (20 ml), 5N-sodium hydroxide (5.7 ml) and benzyl triethyl ammonium chloride (25 mg) were added thereto, and the mixture was allowed to react for 3 hours at room temperature after addition of dimethyl sulfate (1.07 ml) with stirring. The chloroform layer was separated, washed with water and evaporated. As an oil, 3-ethyl-4-chloro-5-(N-acetyl-N-methyl-)aminoisoxazole (3) (990 mg) was obtained.

(iii) Compound (3) (990 mg), 90% methanol (10 ml) and sodium hydroxide (400 mg) were refluxed for 1 hour, evaporated to remove methanol and extracted with chloroform. The extract was washed with water, dried and evaporated to give 3-ethyl-4-chloro-5-methylaminoisoxazole (4) (727 mg) as an oil, mp. 28°–29° C. (recrystallized from cold hexane).

(iv) To a mixture of Compound (4) (660 mg), dimethylformamide (6 ml) and powdered potassium hydroxide (1.34 g) was added 2-propynyl bromide (0.44 ml) under ice-cooling. The mixture was stirred for 30 minutes under ice-cooling and then for 30 minutes at room temperature, neutralized after addition of water and extracted with ether. The extract was washed with water and evaporated. The resulting oily residue was subjected to column chromatography on silica gel (12 g). Oily 3-ethyl-4-chloro-5-(N-methyl-N-propynyl- (i) 3-Phenyl-5-acetylaminoisoxazole (7) (2.022 g) was dissolved in tetrahydrofuran (50 ml), a solution of chlorine (850 mg) in carbon tetrachloride (8.8 ml) was added dropwise thereto, and the mixture was kept to react at room temperature and under ice-cooling for 30 minutes, respectively. After evaporation the resulting residue was subjected to column chromatography on silica gel (20 g) to give crystals (1.43 g) of 3-phenyl-4-chloro-5-acetylaminoisoxazole (8) from the ether fractions; mp. 141°–141.5° C. (recrystallized from ether-hexane).

(ii) Compound (8) (947 mg) was dissolved in anhydrous dimethylformamide (8 ml), 60% sodium hydride (176 mg) was added thereto at room temperature with stirring and the mixture was kept to react at 50° C. for 1 hour. The mixture was further kept to react at room temperature for 1 hour after addition of ice-cooled 2-propynyl bromide (523 mg) and evaporated to remove the solvent. The resulting residue was extracted with chloroform after addition of water. The extract was washed with water, dried, and evaporated. The oily residue was subjected to column chromatography on silica gel (20 g) to yield oily 3-phenyl-4-chloro-5-(N-acetyl-N-2-propynyl)aminoisoxazole (9) (790 mg) (from the methylene chloride fractions).

(iii) The same operation as in Example 1 (iii) was effected with Compound (9) (200 mg) to give 3-phenyl-4-chloro-5-(2-propynyl)aminoisoxazole (10); mp. 83°–84° C. recrystallized from ether-hexane).

(iv) Compound (10) was treated in the same manner as in Example 1 (v) to give 3-phenyl-4-chloro-5-(3-iodo-2-propynyl)aminoisoxazole (11) as crystals (32 mg); mp. 133°–135° C. (recrystallized from ether-hexane).

EXAMPLES 3–31

The same operation as in Example 1 or 2 gave the compounds as follows:

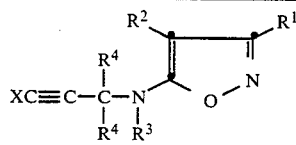

| Ex. No. | R¹ | R² | R³ | R⁴ | X = H NMR $\delta^{CDCl_3}$ (J = Hz) | X = I, mp (°C.) or NMR $\delta^{CDCl_3}$ (J = Hz) | |
|---|---|---|---|---|---|---|---|
| 3 | Me | H | Me | H | 2.13s, 2.32t(J = 2), 2.96s, 4.00d(J = 2), 4.73s | 120–122 | (Comp. 3) |
| 4 | " | " | Et | " | 1.20t(J = 7), 2.27t(J = 2), 3.40q(J = 7), 4.00d(J = 2), 4.87s | 65–66 | (Comp. 4) |
| 5 | Et | " | Me | " | 1.20t(J = 7), 2.30t(J = 2), 2.53q(J = 7), 2.93s, 3.98d(J = 2), 4.90s | 69–70 | (Comp. 5) |
| 6 | i-Pr | " | " | " | 1.22d(J = 7), 2.27t(J = 2), 2.95s, 4.00d(J = 2), 4.90s | 87–88 | (Comp. 6) |
| 7 | t-Bu | " | " | " | 1.27s, 2.27t(J = 2), 2.97s, 4.02d(J = 2), 4.93s | 91–92 | (Comp. 7) |
| 8 | c-Py | " | " | " | 0.93m, 1.88m, 2.31t(J = 2), 2.97s, 4.02d (J = 2), 4.73s | 96–98 | (Comp. 8) |
| 9 | c-He | " | " | " | 1.27–2.06m, 2.30t(J = 2), 2.6m, 3.00s, 4.03d (J = 2), 4.92s | 81–82 | (Comp. 9) |
| 10 | Fu | " | " | " | 2.27t(J = 2), 3.00s, 4.08d(J = 2), 5.30 s, 6.43d-d(J = 4,2), 6.77d(J = 4), 7.45d(J = 2) | 97–99 | (Comp. 10) |
| 11 | 2-Th | " | " | " | 2.28t(J = 2), 2.99s, 4.00d(J = 2), 5.27s, 7.00m, 7.27m, 7.33m | 107–108 | (Comp. 11) |
| 12 | 2-I—4-Th— | " | " | " | — | 165–167(d) | (Comp. 12) |
| 13 | Ph | " | " | " | 2.27t(J = 2), 2.97s, 4.00d(J = 2), 5.31s, 7.33m, 7.73m | 133–134 | (Comp. 13) |
| 14 | 2,4-diCl—Ph | " | " | " | 2.32t(J = 2), 3.05s, 4.08d(J = 2), 5.47s, 7.4m | 107–110 | (Comp. 14) |
| 15 | —(CH₂)₄— | | " | " | 1.67m, 2.33t(J = 2), 2.53m, 3.00s, 3.98d(J = 2) | 137–138 | (Comp. 15) |
| 16 | (Me)₂NCH₂— | H | " | " | 2.28s, 2.28t(J = 2), 3.00s, 3.38s, 4.02d(J = 2), 5.08s | 85–86 (Hydrochloride 158–159(d)) | (Comp. 16) |
| 17 | Im-CH₂— | " | " | " | 2.28s, 2.97s, 4.00d(J = 2), 4.82s, 5.00s, 6.91d(J = 1), 7.02d(J = 1), 7.48brs (Methyl ester) | 128–129(d) (Hydrochloride 150–152(d)) | (Comp. 17) |
| 18 | 3-HOOC—Ph—CH₂O | " | " | " | 2.28(J = 2), 2.97s, 3.85s, 3.98d(J = 2), 4.92s, 5.12s, 7.13br, 7.53br | 147–188 (Sodium salt 165–167(d)) | (Comp. 18) |
| 19 | Me | Me | H | " | 1.77s, 2.10s, 2.27t(J = 2), 4.10br, 4.10br mp 107–8° C. | 130–132 | (Comp. 19) |
| 20 | " | " | Me | " | 1.93s, 2.10s, 2.30t(J = 2), 3.02s, 4.02d(J = 2) | 110–112 | (Comp. 20) |
| 21 | " | " | Et | " | 1.20t(J = 7), 2.30t(J = 2), 3.43q(J = 7), 4.00d(J = 2) | 87–88 | (Comp. 21) |
| 22 | " | MeO | Me | " | 2.15s, 2.25t(J = 2), 3.02s, 3.65s, 4.07d(J = 2) | 107–110(d) | (Comp. 22) |
| 23 | " | (Me)₂NCH₂ | " | " | 2.13s, 2.18s, 2.30t(J = 2), 3.12s, 3.12s, 4.36d(J = 2) | 108–110(d) (Oxalate 85–90(d)) | (Comp. 23) |
| 24 | " | Cl | " | " | 2.12s, 2.35t(J = 2), 3.12s, 4.20d(J = 2) | 113–114 | (Comp. 24) |
| 25 | " | Me | " | Me | 1.42s, 1.85s, 2.17s, 2.37s, 2.85 | 122–123 | (Comp. 25) |
| 26 | i-Pr | Cl | " | H | 1.27d(J = 7), 2.32t(J = 2), 2.93m, 3.12s, 4.17d(J = 2) | 1.28(J = 7), 2.92m, 3.10s, 4.32s | (Comp. 26) |
| 27 | Ph | " | " | " | 2.33t(J = 2), 3.15s, 4.20d(J = 2), 7.33m, 7.7m | 89–90 | (Comp. 27) |
| 28 | " | Me | " | " | 2.30t(J = 2), 3.07s, 4.05d(J = 2), 7.5m | 119–120.5 | (Comp. 28) |
| 29 | " | " | Et | " | 1.23t(J = 7), 2.28t(J = 2), 3.49q(J = 7), 4.07d(J = 2), 7.47m | 186–187 | (Comp. 29) |
| 30 | " | " | Bu | " | 1–1.8m, 2.27t(J = 2), 3.40t(J = 7), 4.03d(J = 2), 7.37m | 1–1.8m, 3.38t(J = 7), 4.18s, 7.47m | (Comp. 30) |
| 31 | MeOCH₂— | " | Me | " | | 61–63 | (Comp. 31) |

Notes:
The abbreviations in the above table each has the following meaining:
Me = Methyl, Et = Ethyl, i-Pro = Isopropyl, Bu = Butyl, t-Bu = Tertiary butyl, c-Pr = Cyclopropyl, c-He = Cyclohexyl, Fu = 2-Furyl, Th = Thienyl, Im = Imidazolyl, Ph = Phenyl.

EXAMPLE 32

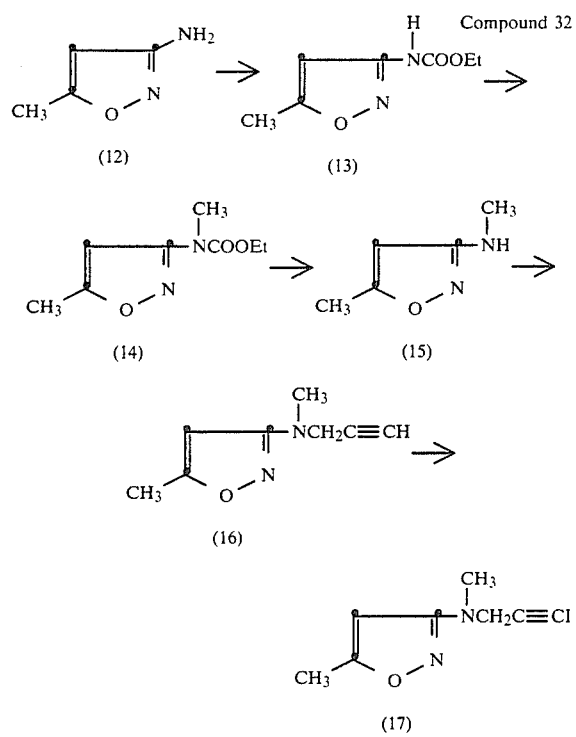

(i) 3-Amino-5-methylisoxazole (12) (9.81 g) was dissolved in benzene (150 ml), ethyl chlorocarbonate (10.5 ml) and successively pyridine (10.3 ml) were added dropwise thereto and the mixture was stirred at room temperature for 2 hours. The reaction mixture was extracted with benzene after addition of 5% hydrochloric acid. The extract was washed with water, dried and evaporated to give crystalline residue (9.8 g). Recrystallization from ether-hexane gave 3-ethoxycarbonylamino-5-methylisoxazole (13) (8.6 g); mp. 90°–91° C.

(ii) Compound (13) (4.55 g) was dissolved in dimethyl formamide (30 ml), wherein 50% sodium hydride (1.28 g) was added with stirring under ice-cooling and after heating of the mixture at 50° C. for 1 hour, methyl iodide (2.17 ml) was added dropwise under ice-cooling. The reaction mixture was kept to react at room temperature for 1 hour and then water was added thereto. The precipitated crystals were obtained by filtration and washed with water to give 3-(N-ethoxycarbonyl-N-methyl)amino-5-methylisoxazole (14) (4.25 g); mp. 39°–39.5° C.

(iii) Compound (14) (3.25 g), 80% methanol (20 ml) and sodium hydroxide (1 g) were refluxed for 1 hour and evaporated to remove the solvent. The resulting residue was extracted with chloroform. The extract was washed with water, dried and evaporated to give 3-methylamino-5-methylisoxazole (15) (2.12 g). Recrystallization from ether-hexane gives crystals melting at 53°–54° C.

(iv) Compound (15) (305 mg) was dissolved in anhydrous tetrahydrofuran (10 ml), a solution of butyllithium (226 mg) in hexane (2.51 ml) was added thereto at −70° C. with stirring under a nitrogen atmosphere and the mixture was maintained to react at the same temperature for 1 hour and 30 minutes. The reaction mixture was further maintained to react at −70° C. for 1 hour after dropwise addition of 2-propynyl bromide (0.31 ml), then permitted to stand at room temperature overnight and evaporated. The resulting residue was extracted with ether after addition of water. The extract was washed with water, dried and evaporated. The oily residue was subjected to column chromatography on silica gel (10 g) to yield oily 3-(N-methyl-N-2-propynyl)amino-5-methylisoxazole (16) (193 mg). NMR$\delta_{CDCl_3}$ 2.23 (J=2 HZ), 2.30s, 2.93s, 3.93d (J=2), 5.58s.

(v) Compound (16) (193 mg) was dissolved in anhydrous tetrahydrofuran (10 ml), a solution of butyllithium (107 mg) in hexane (1.18 ml) was added at −70° C. with stirring under a nitrogen atmosphere and the mixture was kept to react at −70° C. for 1 hour and 30 minutes. The reaction mixture was further permitted to react at −70° C. for 10 minutes after the addition of iodine (425 mg) and at room temperature for 30 minutes and evaporated to remove the tetrahydrofuran. The resulting residue was extracted with chloroform after the addition of water. The extract was washed with water, dried and evaporated. The resultant residue was subjected to column chromatography on silica gel (6 g) to yield crystalline 3-(N-methyl-N-3-iodo-2-propynyl)amino-5-methylisoxazole (17) (192 mg) (from the chloroform fractions). Recrystallization from ether-hexane gives crystals melting at 86°–86.5° C.

Elementary Analysis: Anal. Calcd. for $C_8H_9N_2OI$: Calcd.(%):C,34.80; H, 3.29; N, 10.15; I, 45.97. Found(%):C, 34.85; H, 3.26; N, 10.05; I, 45.76.

EXAMPLE 33

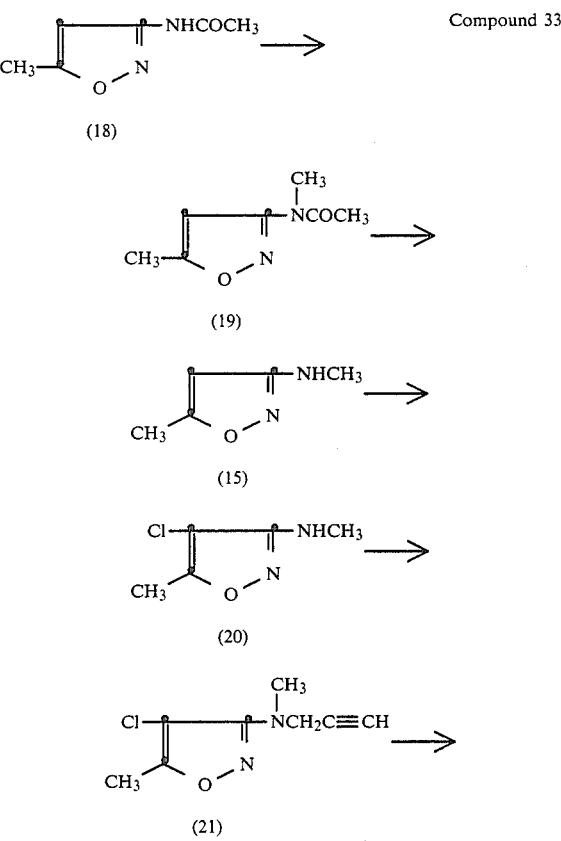

-continued

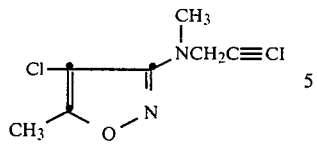

(22)

(i) 3-Acetylamino-5-methylisoxazole (18) (56.05 g) was treated in the same manner as in Example 1 (ii) and (iii) to give 3-methylamino-5-methylisoxazole (15) (40.13g).

(ii) Compound (15) (19.06 g) was dissolved in methylene chloride (150 ml) and a solution of chlorine (13.1 g) in carbon tetrachloride (139 ml) was added thereto dropwise. The mixture was stirred at room temperature for 10 minutes, then washed with a 50% potassium carbonate solution and water, dried and evaporated to give 3-methylamino-4-chloro-5-methylisoxazole (20) (21.07 g); mp. 43°–47° C.

(iii) Compound (20) (21 g) was treated in the same manner as in Example 1 (iv) to give 3-(N-2-propynyl-N-methyl)-amino-4-chloro-5-methylisoxazole (21) (22.0) as an oil. NMR$\delta_{CDCl_3}$ 2.27s, 2.27t (J=2), 2.97s, 4.10d (j=2).

(iv) Compound (21) (351 mg) was treated in the same manner as in Example 1(v) to give 3-(N-methyl-N-3-iodo-2-propynyl)amino-4-chloro-5-methylisoxazole (22) (516 mg).

Elementary Analysis: Calcd. for $C_8H_8N_2OClI$; Calcd.(%):C, 30.94; H, 2.60; N, 9.02; I, 40.87; Cl, 11.42, Found (%):C, 30.73; H, 2.84; N, 9.03; I, 40.61Cl, 11.06.

Mp. 87°–87.5° C. (recrystallized from ether-hexane).

EXAMPLE 34

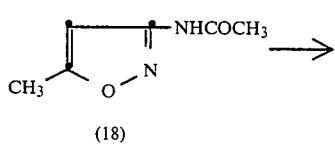  Compound 34

(18)

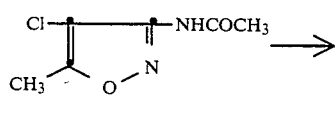

(23)

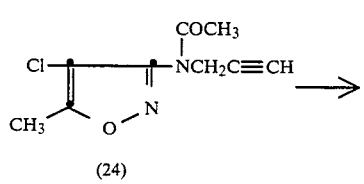

(24)

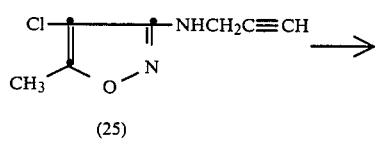

(25)

-continued

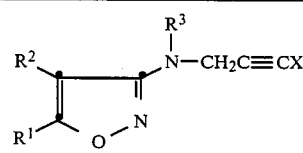

(26)

(i) 3-Acetylamino-5-methylisoxazole (18) (1.79 g) was treated in the same manner as in Example 33 (ii) to give 3-acetylamino-4-chloro-5-methylisoxazole (23) (1.503 g); mp. 121°–122° C.

(ii) Compound (23) (920 mg) was dissolved in methylene chloride (16 ml) and there was added 5N sodium hydroxide (10 ml) and benzyl triethyl ammonium chloride (40 mg) under ice-cooling with stirring and then 2-propynyl bromide (0.564 ml) with stirring. The mixture was allowed to react at room temperature for 3 hours and extracted with chloroform. The extract was washed with water, dried and evaporated. The resulting residue was subjected to column chromatography on silica gel (15 g) to yield 3-(N-acetyl-N-2-propynyl-)amino-4-chloro-5-methylisoxazole (24) as an oil (518 mg).

(iii) Compound (24) (518 mg) was treated in the same manner as in Example 1 (iii) to give 3-(2-propynyl)-amino-4-chloro-5-methylisoxazole (25) as crystalline residue; mp. 65°–65.5° C. (recrystallized from ether-hexane).

(iv) Compound (25) (293 mg) was treated in the same manner as in Example 1 (v) to give 3-(3-iodo-2-propynyl)-amino-4-chloro-5-methylisoxazole (26) (438mg); mp. 137°–138° C. (decomp.) (recrystallized from ether-hexane).

Elemantary Analysis: Calcd. for $C_7H_6N_2OClI$: Calcd.(%): C, 28.36; H, 2.04; N, 9.45; Cl, 11.96; I, 42.80, Found (%): C, 28.16; H, 2.24; N, 9.36; Cl, 11.71; I, 42.57.

EXAMPLES 35–37

The same operation as in Example 33 gave the following compounds:

| Ex. No. | $R^1$ | $R^2$ | $R^3$ | X = H NMR $\delta_{CDCl_3}$ (J = Hz) | X = I Mp. (°C.) or NMR $\delta_{CDCl_3}$ (J = Hz) |
|---|---|---|---|---|---|
| 35 | Me | H | Et | 1.17t(J = 7), 2.2t(J = 2) 2.3s, 3.37q(J = 7), 4.0d(J = 2), 5.63s | 1.17t(J = 7), 2.28s, 3.35q(J = 7), 4.13s, 5.62s (Compound 35) |
| 36 | Ph | Me | Me | 2.18s, 2.32t(J = 2) 4.02d(J = 2), 7.47m | 123–125 (Compound 36) |
| 37 | Ph | Me | Et | 1.2t(J = 7), 2.13s, 2.27t(J = 2), 3.42q (J = 7), 4.02d(J = 2), 7.47m | 72–73 (Compound 37) |

EXAMPLE 38

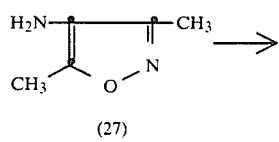

Compound 38

(27)

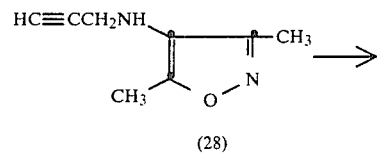

(28)

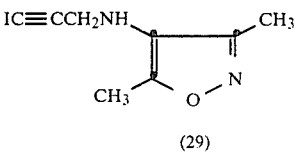

(29)

(i) A mixture of 3,5-dimethyl-4-aminoisoxazole (27) (600 mg), tetrahydrofuran (6 ml) and 2-propynyl bromide (0.45 ml) was stirred at 70° C. for 25 hours, evaporated to remove the tetrahydrofuran and extracted with chloroform after being made alkaline with 5% potassium carbonate. The extract was washed with water, dried and evaporated. The oily residue was subjected to column chromatography on silica gel (12 g) to give 3,5-dimethyl-4-(2-propynyl)aminoisoxazole (28) (325 mg) as an oil (from the chloroform fractions). NMR$\delta_{CDCl_3}$ 2.20s, 2.27t (J=2), 2.35s, 2.67br, 3.65br.

(ii) Compound (28) (405 mg), methanol (6 ml), water (2 ml) and potassium hydroxide (518 mg) were stirred at room temperature for 30 minutes and iodine (1.1 g) was added thereto. The mixture was stirred for 1 hour and evaporated. The resulting residue was extracted with chloroform after addition of a sodium thiosulfate solution. The extract was washed with water, dried and evaporated. The resultant residue was subjected to column chromatography on silica gel (10 g) to yield 3,5-dimethyl-4-(3-iodo-2-propynylamino)isoxazole (29) (150 mg); mp. 139°-140° C.

Elementary Analysis: Calcd. for $C_8H_9N_2OI$: Calcd.(%):C,34.80; H, 3.29; N, 10.15; I, 45.97 Found (%):C,35.00; H, 3.30; N, 9.89; I, 45.58

EXAMPLE 39

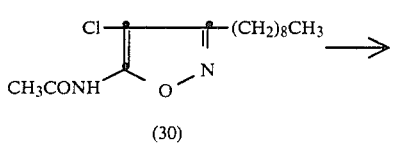

Compound 39

(30)

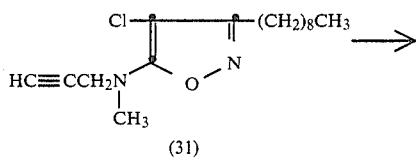

(31)

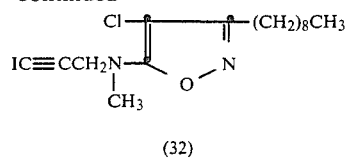

(32)

3-Nonyl-4-chloro-5-acetylaminoisoxazole (30) was treated in the same manner as in Example 1 to give 3-nonyl-4-chloro-5-(N-methyl-N-2-propynyl-)aminoisoxazole (31) (NMR$\delta_{CDCl_3}$ 1.18 m, 1.27m, 2.3t (J=2 Hz), 2.35m, 3.13s, 4.2d (J=2)) and 3-nonyl-4-chloro-5(N-methyl-N-3-iodo-2-propynyl)aminoisoxazole (32); Mp. 39° C.

EXAMPLE 40

Five parts (which means weight to weight ratio throughout the Examples) of the hydrochloride of Compound 1, 20 parts of propylene alcohol, 5 parts of polyoxyethylene alkyl phenyl ether and 70 parts of water were mixed and dissolved to give an aqueous solution. The solution was diluted with water so that the effective concentration of Compound 1 was 50–500 ppm and sprayed onto the leaves and stems of the subject.

EXAMPLE 41

Fifty parts of Compound 5, 6 parts of sodium alkylbenzene sulfonate, 4 parts of sodium lignin sulfonate and 40 parts of clay were mixed and smashed to produce a wettable powder. The powder was diluted with water so that the effective concentration of Compound 5 was 50–500 ppm and sprayed onto fruit.

EXAMPLE 42

Five parts of Compound 11, 90 parts of an equivalent mixture of bentonite and talc and 5 parts of sodium alkylbenzene sulfonate were mixed, smashed and formulated to granules.

EXAMPLE 43

Twenty-five parts of Compound 19, 8 parts of polyoxyethylene alkyl phenyl ether, 2 parts of sodium alkylbenzene sulfonate and 65 parts of xylene were mixed and dissolved to give concentrated emulsion. The emulsion was diluted with water so that the effective concentration of Compound 19 was 50–500 ppm and sprayed onto leaves and stems.

EXAMPLE 44

One part of Compound 33 was added to 99 parts of talc to produce a powder.

EXAMPLE 45

Three parts of Compound 1, 25 parts of white vaseline, 25 parts of stearyl alcohol, 12 parts of propylene glycol, 1.5 parts of sodium lauryl sulfate, 0.025 parts of ethyl p-hydroxybenzoate, 0.015 parts of propyl p-hydroxybenzoate and the balance of water (total 100 parts) were mixed to produce an ointment.

EXAMPLE 46

A hundred parts of Compound 24, 50 parts of a mixture of hydroxypropyl starch, crystalline cellulose and aluminium silicate (60:20:20) were mixed and formulated into tablets.

EXAMPLE 47

Five parts of Compound 2 was dissolved in peanut oil to produce an injectable solution.

EXAMPLE 48

Ten parts of Compound 15 and 90 parts of lactose were well mixed to produce 10-fold powder, which was diluted with feed at a concentration of 0.001–0.05% of the effective active ingredient.

While a preferred embodiment of the invention has been described in specific terms, such description is for illustrative purposes only, and it is to be understood that changes and variations may be made without departing from the spirit and scope of the following claims.

What we claim is:

1. A compound of the formula I:

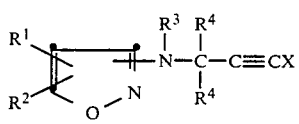

wherein $R^1$ and $R^2$ each is hydrogen, $C_1$–$C_{10}$ alkyl, $C_1$–$C_4$ alkoxy, $C_3$–$C_6$ cycloalkyl, halogen, A—$CH_2$—, B—, B—$CH_2$— or B—$CH_2O$— wherein A is $C_1$–$C_4$ alkoxy or mono- or di- $C_1$–$C_4$ alkylamino and B is phenyl, furyl, thienyl or imidazolyl optionally substituted by one or two groups selected from the group consisting of halogen and carboxy;

$R^1$ and $R^2$ when taken together may form $C_2$–$C_5$ alkylene;

$R^3$ and $R^4$ each is hydrogen or $C_1$–$C_4$ alkyl; and X is iodine.

2. The compound claimed in claim 1 wherein $R^1$ is $C_1$–$C_{10}$ alkyl, $C_3$–$C_6$ cycloalkyl or optionally substituted phenyl or thienyl.

3. The compound claimed in claim 1 wherein $R^2$ is hydrogen, $C_1$–$C_4$ alkyl or halogen.

4. The compound claimed in claim 1 wherein $R^3$ is hydrogen, methyl or ethyl.

5. The compound claimed in claim 1 wherein $R^4$ is hydrogen.

6. The compound claimed in claim 2 wherein $R^1$ is $C_1$–$C_4$ alkyl.

7. The compound claimed in claim 2 wherein $R^2$ is hydrogen, $C_1$–$C_4$ alkyl or halogen.

8. The compound claimed in claim 7 wherein $R^3$ is hydrogen, methyl or ethyl.

9. The compound claimed in claim 8 wherein $R^4$ is hydrogen.

10. The compound claimed in claim 9 wherein $r^3$ is methyl

11. The compound claimed in claim 9 wherein $R^1$ is $C_1$–$C_4$ alkyl.

12. The compound claimed in claim 9 wherein $R^1$ is phenyl.

13. The compound claimed in claim 9 wherein $R^1$ is thienyl.

14. The compound claimed in claim 9 wherein the group

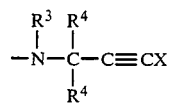

is located at the position 3 of the isoxazole ring.

15. The compound claimed in claim 9 wherein the group

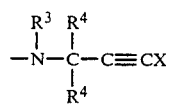

is located at the position 5 of the isoxazole ring.

16. An anti-microbial composition for medical use which comprises an anti-microbially effective amount of a compound claimed in claim 1 as an active ingredient with pharmaceutically acceptable adjuvants.

17. An anti-microbial composition for agricultural use which comprises an effective amount of a compound claimed in claim 1 as an active ingredient with agriculturally acceptable adjuvants.

18. An anti-microbial composition for veterinary use which comprises an effective amount of the compound claimed in claim 1 as an active ingredient with adjuvants suitable for veterinary use.

19. The compound claimed in claim 1, viz., 5-methyl-3-[N-methyl-N-(3-propargyl)amino]-isoxazole.

20. The compound claimed in claim 1, viz., 4-chloro-3-(3-iodopropargyl)amino-5-methyl-isoxazole.

21. The compound claimed in claim 1, viz., 4-chloro-5-methyl-3-[N-methyl-N-(3-iodopropargyl)amino]-isoxazole.

* * * * *